United States Patent [19]
Sato et al.

[11] 4,000,072
[45] Dec. 28, 1976

[54] ARTIFICIAL KIDNEY APPARATUS

[75] Inventors: Hiroshi Sato; Teruhisa Kidaka, both of Hyogo; Yasuhiro Tsujimoto; Nobuo Nakamura, both of Osaka, all of Japan

[73] Assignee: Takeda Chemical Industries, Ltd., Osaka, Japan

[22] Filed: Sept. 6, 1974

[21] Appl. No.: 503,923

[30] Foreign Application Priority Data

Sept. 19, 1973 Japan .................... 48-105804

[52] U.S. Cl. .............................. 210/315; 210/317; 210/321 B; 210/494 M
[51] Int. Cl.² ...................................... B01D 31/00
[58] Field of Search ........... 210/321, 494, 315, 317

[56] References Cited
UNITED STATES PATENTS

| | | | |
|---|---|---|---|
| 3,357,563 | 12/1967 | Sicard | 210/315 X |
| 3,503,515 | 3/1970 | Tomsic | 210/321 |
| 3,608,729 | 9/1971 | Haselden | 210/321 |
| 3,703,959 | 11/1972 | Raymond | 210/321 X |
| 3,742,946 | 7/1973 | Grossman | 210/321 X |
| 3,853,769 | 12/1974 | Miller | 210/494 X |
| 3,884,808 | 5/1975 | Scott | 210/321 X |

*Primary Examiner*—Frank A. Spear, Jr.
*Attorney, Agent, or Firm*—Wenderoth, Lind & Ponack

[57] ABSTRACT

An artificial kidney apparatus has a dialysing unit including a blood chamber or chambers and a dialysate chamber or chambers disposed adjacent said blood chamber across a semipermeable membrane or membranes. An adsorbent chamber is centrally positioned with the dialysate chamber therearound or vice versa. The dialysing unit is removably mounted in a fluid tank, and a means is provided for circulating the dialysate within the fluid tank.

11 Claims, 5 Drawing Figures

ARTIFICIAL KIDNEY APPARATUS

The present invention relates to an artificial kidney apparatus which has been significantly reduced in size and made portable. In recent years dialysis of blood has been widely practiced, and has by now become essential, for patients with chronic uremia or acute renal failure or cases of drug intoxication. The hemodialysis most commonly practiced today employs a semipermeable membrane, which is commonly a cellophane membrane, and a dialysate fluid. The blood is cleaned by passing the arterial blood of the patient against the dialysate fluid across the cellophane membrane so that the uremic wastes in the blood, such as urea, uric acid, creatinine, etc., are caused to pass across the membrane into the dialysate fluid on account of the concentration gradient between the blood and dialysate.

Heretofore, all the dialysate fluid which has once been subjected to dialysis has been discarded and a fresh supply of dialysate fluid is continuously provided. However, dialyzing systems of this type have the disadvantage that because the dialysate fluid must thus be constantly replenished, a prohibitive large volume of dialysate fluid is of necessity consumed. The results are high costs of dialysis and a relatively large space required for dialysis apparatus.

The idea has recently been advanced to use an adsorbent material to remove the uremic wastes while recycling the dialysate fluid and thus to reuse the recycled dialysate, thereby reducing the amount of dialysate fluid required and making the artificial kidney system smaller in size, easier to use and less expensive. One dialyzing unit for an artificial kidney apparatus has already been proposed which has a sleeve in the form of a dialyzer, such as a coil tube type dialyzer, or a capillary tube type dialyzer, disposed around a generally cylindrical container of an adsorbent material as a core. Alternatively the container can be the sleeve and the dialyzer the core. This dialyzing unit is designed to be placed in a fluid tank and a means can then be provided for circulating the fluid to fluid tank and through the dialyzing unit.

However, the structure of this dialyzer unit is limited so that the dialysate flows through the core and the sleeve, or vice versa, in series, and while this is suitable for many situations, there are other situations where it would be desirable to cause the flow to flow through the dialysis unit differently.

It is therefore an object of the present invention to provide a dialyzer unit having a core and sleeve which are a dialyzer and a container of adsorbent, and in which the flow of dialysate is branched so as to flow simultaneously through the core and the sleeve so that dialysate is being passed through the dialyzer for carrying out dialysis and dialysate is also being passed through the adsorbent for removal of the contaminants.

It is also an object of the invention to provide a dialysis apparatus which includes the dialyzer unit of the invention and means for directing the flow of dialysate in a tank system in which the dialyzer unit of the invention is positioned.

The artificial kidney apparatus of the present invention will hereinafter be described in further detail, reference being made to several views of the accompanying drawing, in which.

Figure 1:
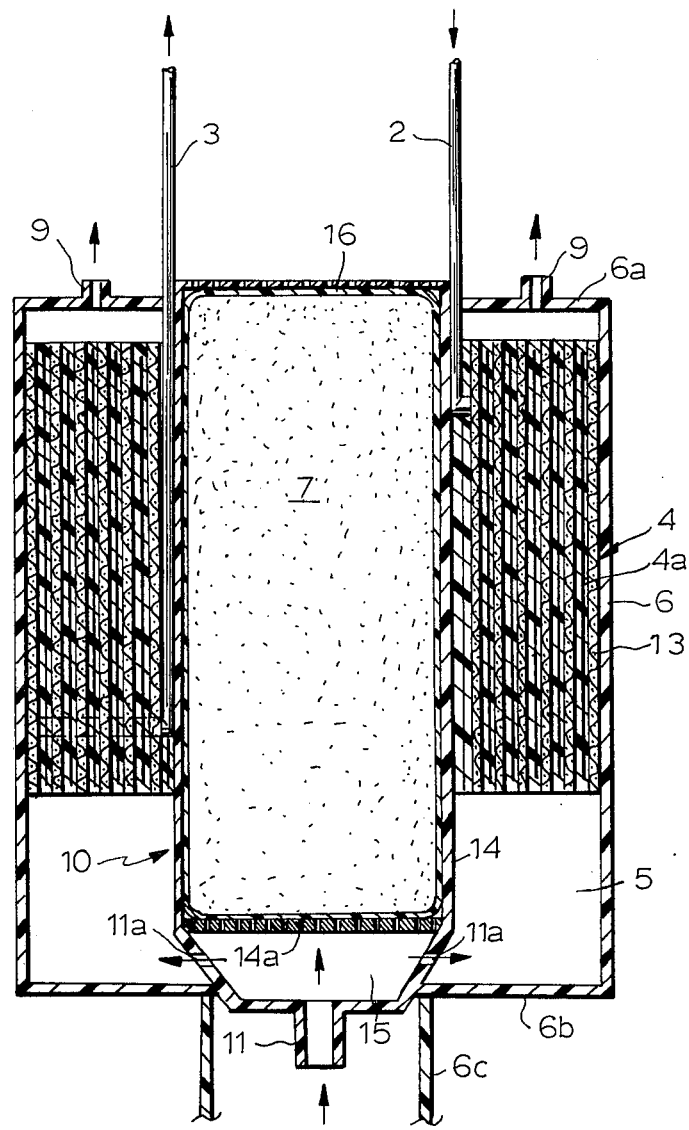
FIG. 1 is a schematic sectional view of one embodiment of the dialyzing unit of the present invention.

Referring now to FIG. 1, a generally cylindrical adsorbent chamber 10 containing an adsorbent material 7 forms a core. Around the core is a sleeve which is a dialyzer 4, which in this embodiment is a coil tube type dialyzer having a tubular semipermeable membrane 4a and a plastic mesh sheeting 13 wound in alternating layers. A space 5 is defined between an outer cylinder 6 and a cylinder wall 14 forming the core and which is closed by end walls 6a and 6b connected to inner cylinder wall 14. Support member 6c depends from end wall 6b. The blood is introduced through an inlet 2 connected to one end of the tubular membrane 4a and the dialyzed blood is discharged from an outlet 3 connected to the other end of the tubular membrane 4a. On the bottom of the adsorbent chamber 10 is a dialysate distribution chamber 15 defined by the extension of wall 14 and end wall 6b. Dialysate inlet 11 opens into distribution chamber 15. Apertures 11a 11a from the distribution chamber 15 to space 5, and outlets 9 are provided in end wall 6a at the top of the sleeve. A porous wall 14a closes the bottom of chamber 10. Adsorbent material 7 is contained in a porous membrane 16 and substantially fills chamber 10.

In operation, the dialysate enters through the dialysate inlet 11 into the distribution chamber 15, wherein a portion of dialysate is directed into space 5 and the remainder into adsorbent chamber 10. THe dialysate, after flowing through the adsorbent 7, overflows at the top. The dialysate directed into the space 5 flows along the faces of tubular membrane 4a dialyzing the blood and, then, overflows through the dialysate outlet 9.

Figure 2:
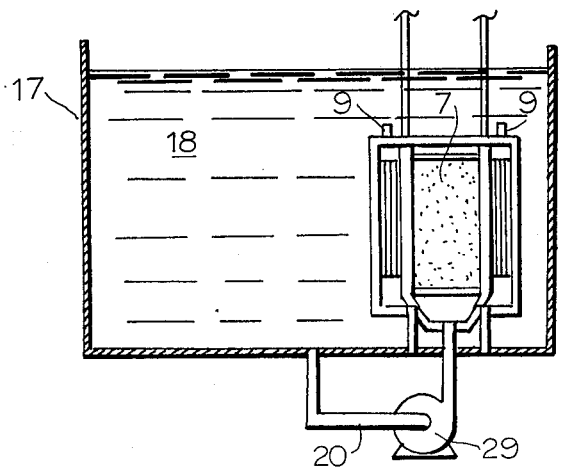
FIG. 2 is a diagrammatic view of the artificial kidney apparatus of this invention.

As illustrated in FIG. 2, such a unit can be installed in a fluid tank 17, and the dialysate 18 overflowing from chamber 10 and outlets 9 flows into the body of dialysate in fluid tank 17. Pump means 29 draws dialysate from the tank and pumps it through pipe 20 to the dialysis unit. The dialysis unit can be removably installed in the fluid tank and, after use, either the entire unit or the adsorbent material 7 and the membrane in which it is enclosed alone can be discarded.

With this arrangement, it is possible, by correctly sizing the apertures 11a and porous wall 14a to control the rates of flow of dialysate through the adsorbent 7 and over the dialysis tube of the dialyzer 4 to the most desirable rates. It is often the case that the rate of flow through the adsorption material 7 to achieve optimum adsorption is less than that for flow of the dialysate over the tubular membrane 4a to achieve optimum dialysis. By utilizing the structure as described above for FIGS. 1 and 2, the optimum flow rates for both flows can be achieved in the same apparatus.

Figure 3:
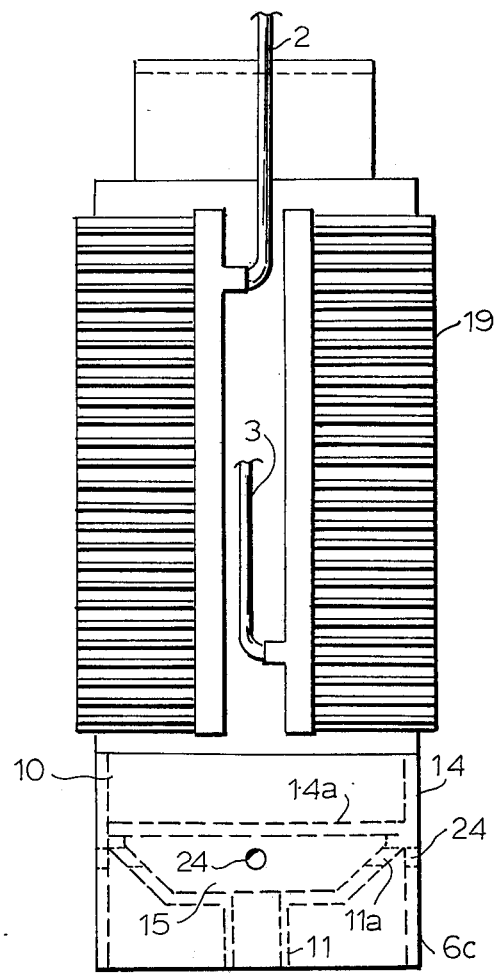
FIG. 3 is a side elevation view of still another embodiment of the dialyzing unit of the present invention in which hollow-fiber semipermeable membranes are used.

The unit illustrated in FIG. 3 is similar to that of FIGS. 1 and 2 and is designed to be used in substantially the same way. It has the core with the cylinder wall 14 on the lower end of which is the porous wall 14a and which contains the adsorbent. The support member 6c depends from the cylinder wall 14 and the apertures 11a open laterally out of the distribution chamber 15, in this instance in four directions. In the particular construction illustrated, the wall of the cylinder defining the distribution chamber is spaced slightly inwardly of the support member 6c, so that the apertures must be extended at 24 through the support member 6c. The dialyzer in this embodiment is a capillary tube type dialyzer 19 in which the tubes are wrapped around the core. The flexible blood inlet tube 2 extends from the inlet and the flexible blood outlet tube 3 extends from the outlet.

The use of the unit of FIG. 3 is the same as that of FIG. 1. It is stood in a tank as shown in FIG. 2 in the same manner as the unit of FIG. 1, and the dialysate is pumped into the inlet 11. The flow of the dialysate through the adsorber is the same as for the unit of FIG. 1. However, when the unit of FIG. 3 is stood by itself in the tank, flow of the dialysate over the dialyzer 19 is by convection currents flowing upwardly along the dialyzer from the openings 24.

If it is desired to improve the flow of dialysate along the sides of the cylinder wall 14 over the tubes of the capillary tube dialyzer 19, a sleeve similar to the outer cylinder 6 can be placed around the capillary dialyzer 19, in which case the unit would be substantially the same as that of FIG. 1 except for the specific form of dialyzer.

In all of the embodiments described thus far, the dialyzer has been positioned as a sleeve around an adsorber which is the core for the dialyzer sleeve. It is clear that the two elements can be reversed, i.e., the dialyzer can be positioned within a sleeve in the form of an adsorber to serve as the core for the adsorber. In the embodiment of FIG. 1, this would simply mean positioning the tube 4a within the chamber 10, and filling the space 5 with the adsorbent 7.

Figure 4:
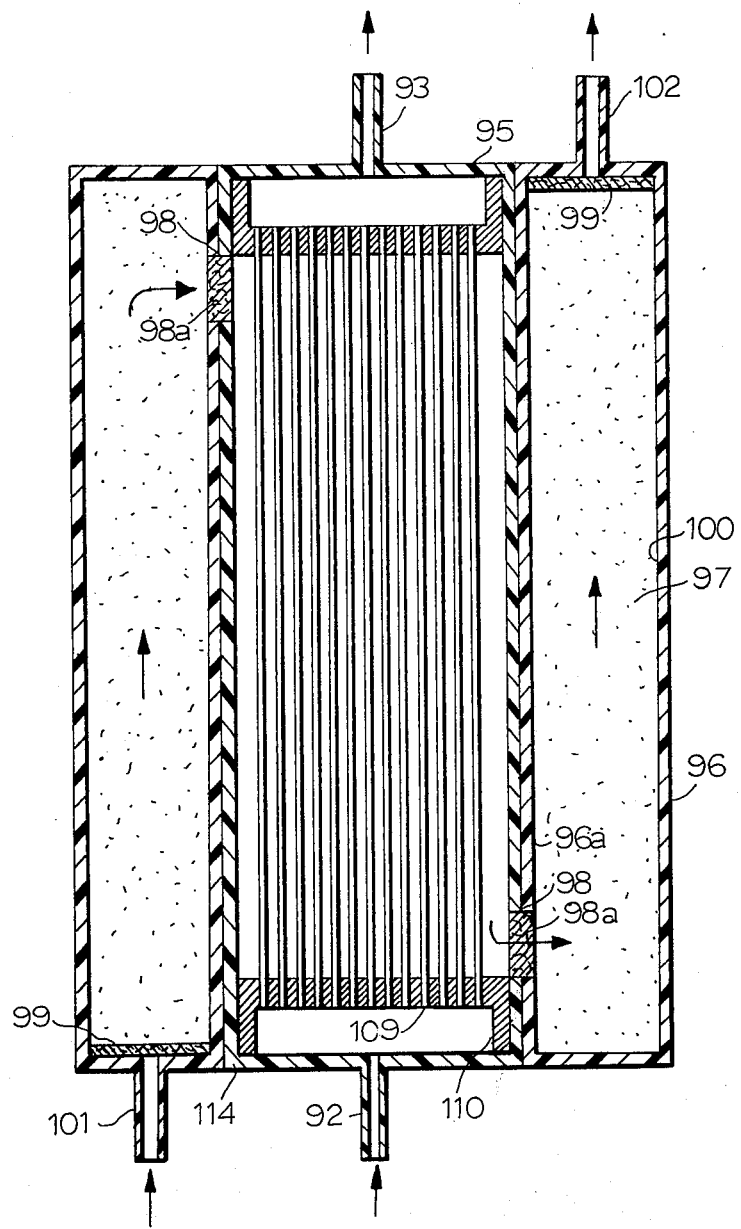
FIG. 4 is a schematic sectional view of another embodiment of the dialyzing unit employing hollow-fiber semipermeable membranes.

A further modification of such an arrangement is shown in FIG. 4. A cylindrical dialysis chamber 95 is provided as a core for the unit and has an outer cylindrical wall 114. Around the dialysis chamber 95 are two matching annular semicylindrical adsorbent chambers 96 having an inner cylindrical wall 96a fitting tightly against the outer cylindrical wall 114. Within the dialysis chamber 95 is a dialyzer which is made up of a plurality of hollow-fiber semipermeable membranes 109 extending parallel to the axis of the cylinder and having the ends mounted on and sealed to mounting members 110 at the opposite ends of the chamber 95. Thus the passages through the fiber membranes 109 constitute passages for the blood being dialyzed, while the space around the membranes 109 within the chamber 95 constitutes a space for the flow of dialysate over the outer surfaces of the membranes 109. A blood inlet 92 is provided at one end of the chamber 95 while a blood outlet 93 is provided at the other end of the chamber 95.

Each of the annular semicylindrical chambers 96 constitutes an adsorbent chamber 100 which is filled with adsorbent 97. A dialysate inlet 101 is provided at one end of one of the adsorbent chambers 100 while a dialysate outlet 102 is provided at the other end of the other adsorbent chamber 100. Filters 99 are for the inlet 101 and outlet 102. At the opposite end of the one adsorbent chamber 100 from the dialysate inlet 101 is a lateral aperture 98 which extends through both the inner wall 96a of the chamber 96 and also through the cylindrical wall 114 of the dialysate chamber 95. This aperture is filled by a filter member 96a. A similar lateral aperture 98 is provided at the other end of the other adsorbent chamber 100 from the dialysate outlet 102, and this is also filled by a filter member 98a.

With this arrangement, blood flowing into the inlet 92 will flow through the hollow fiber membranes 109 and out the outlet 93. This inlet and outlet are of course connected to the source of blood to be dialyzed. Dialysate, on the other hand, is pumped into the unit through inlet 101 whereupon it flows in sequence through the adsorbent in the one annular semicylindrical chamber 100, through the dialysis chamber 95 over the surfaces of the membranes, and then through the adsorbent in the other annular semicylindrical chamber. By placing the first aperture 98 at one end of the dialysis chamber 96 and the second aperture 98 at the other end, flow of the dialysate diagonally across the chamber 95 is insured, thus insuring that the dialysate spends the maximum amount of time in the chamber 95 and that fresh dialysate flows in all parts of this chamber. The dialysate flowing into the unit is first subjected to adsorption before it flows across the membranes, thereby removing any residual impurities therefrom, and is again subject to adsorption immediately after it has flowed over the membranes.

In use this unit can be hooked into a dialysis apparatus in a way generally similar to that shown in FIG. 2 for the embodiment of FIG. 1. The unit is preferably placed in a separate tank from the dialysate, however, and the blood tubes are hooked to the blood inlet 92 and blood outlet 93 respectively.

It will be understood that while only a single dialysate inlet 101 and a single dialysate outlet 102, and single apertures 98 are shown, it is within the scope of the invention to provide a plurality of such openings in order to speed the flow of dialysate and spread it more evenly throughout the apparatus.

The semipermeable membranes employed in the blood dialyzing units thus far illustrated and described, are semipermeable membranes which are able to dialytically remove from the blood various uremic wastes such as urea, creatinine, uric acid, phosphate ions, potassium ions, etc.. For example, cellophane, Cuprophane, cellulose acetate, etc. can be employed. Most generally, the adsorbent to be employed in the artificial kidney apparatus of this invention comprises activated carbon. While the activated carbon which is used for this purpose may be of any type, it is particularly effective to use steam-activated carbon made from sawdust, coal, coconut shells and other materials. Preferably the particle size of the activated carbon is within a size range of about 10 to 200 mesh and, particularly, about 16 to 100 mesh. Further, the carbon is preferably a granular carbon in order to ensure a sufficient particle integrity to prevent entry of fine dust into the dialysate or fragmentation during the operation and, also, to make a large surface area available for adsorption. It is also possible to employ activated carbon paper or fibrous carbon products obtainable by the activation of carbon fibers or carbon fiber webs. Further, as said adsorbent, alumina gel may be used in combination with activated carbon. For example, such alumina gel may be prepared by adding an alkali (e.g., ammonia, calcium carbonate, etc.) to an aqueous solution of an aluminum salt (e.g., aluminum sulfate, aluminum chloride and other mineral acid salts) to neutralize the latter while the resultant salt and other solubles are removed by rinsing to cause an alumina sol to form, maintaining the sol in a hydrophobic medium (e.g., hydrocarbon, halogenated hydrocarbon, spindle oil, etc.) at an elevated temperature (e.g., 70° to 100° C) and thereby ripening it to gel and, finally drying the same. In addition, depending upon the types of metabolic wastes to be adsorbed, use may be made of suitable adsorbents which, if necessary may be employed in a mixture. Such adsorbents can be packed into the unit in amounts depending on such variables as the amount of blood to be dialyzed, and the types and amounts of wastes to be removed from the blood. Furthermore, it is also permissible to incorporate, together with the adsorbent, other agents such as crystals of dialysate constituents, insolubilized enzymes, etc..

The contents of the adsorbent chamber other than those soluble in dialysate, if allowed to emerge in solid condition from the adsorbent chamber, will cause undesirable effects, for it will then be necessary to provide a special type of pump means for the dialysate. It is, therefore, generally preferable to install a filter or equivalent means at each dialysate outlet and inlet.

The fluid tank may be of any type as long as the dialyzing unit can be removably installed therein, and there may also be provided a means for connecting and securing in position a shunt tubing or tubings extending to the blood chamber. While the size of said tank may vary with the volume of blood to be dialyzed, it is usually sufficient to ensure that the tank has a capacity of about 30 liters, which is the volume necessary for an adult patient. If the tank is large enough to accommodate two or more dialyzing units, two or more patients may be simultaneously dialyzed.

The artificial kidney apparatus of the present invention which has thus far been described in detail is advantageous in that by virtue of the positioning of the dialyzing unit within the fluid tank, the apparatus as a whole is made more efficient and compact, can be used repeatedly by mere replacement of the dialyzing unit, is very convenient to operate, can be easily sterilized and disinfected against microbial contaminations and can be employed safely, positively and expediently at hospitals and other clinical establishments.

EXPERIMENT 1

An experimental dialysis of blood was performed using the dialyzing unit illustrated in FIG. 1. The conditions used are as follows:
a. Dialysate fluid: 30 liters [AK Solita (Shimizu Seiyaku Co., Ltd.), 1-in-35 dilution, 37° C]
b. Flow rate of dialysate: 5 liters/min. (semipermeable membrane), 0.5 liters/min. (adsorbent)
c. Simulated blood: The same dialysate supplemented with 17.2 milligrams/dl. of creatinine
d. Flow rate of simulated blood: 200 milliliters/min.
e. Fluid tank and pump means:
   Fluid tank: 40 cm in diameter and 40 cm in height
   Drive means: A snake pump
      Maximum flow: 19 liters/minute (60 cycles)
      Maximum head: 3.0 meters $H_2O$ (60 cycles)
f. Activated carbon: Steam-activated coconut shell granular carbon, 48 to 20 meshes, 500 grams.
g. Semipermeable membrane: Bemberg Cuprophan (trade name of West Germany), 0.8 square meters.
h. Control apparatus: A commercial coil-type dialyzer in combination with a circulation-type dialysate supply unit for artificial kidney use.

Figure 5:
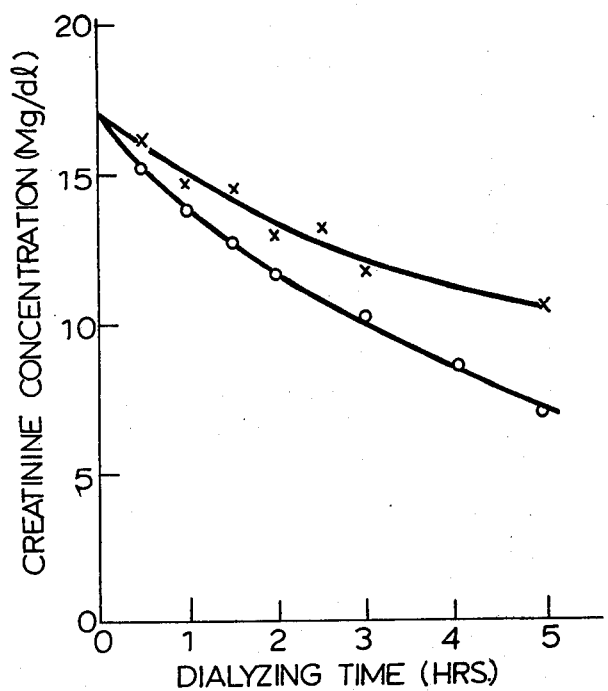
FIG. 5 is a graph showing the results of experimental dialysis performed using the dialyzing unit illustrated in FIG. 1.

The test result is graphically presented in FIG. 5, where the creatinine concentration of the simulated blood on the vertical axis is plotted against the dialyzing time on the horizontal axis.

It will be seen that whereas the control apparatus began to show an attenuation of concentration drop about 3 hours after the start of dialysis (the cross mark), the blood dialysis apparatus of the present invention shows a more constant concentration decrease (the circle mark). Thus, whereas the control apparatus requires a dialyzing time of 5 hours, the apparatus of the present invention achieves the same result in about 2.6 hours.

What is claimed is:
1. A combined dialyzer and adsorber unit comprising a core member and a sleeve member around said core member, one of said members being a dialyzer chamber having a dialyzer therein and a dialysate outlet at one end of the unit, and the other of said members being an adsorbent chamber adapted to contain an adsorbent therein and a dialysate outlet at said one end, and a dialysate distribution chamber on the other end of said unit having a dialysate inlet therein and having apertures opening into said adsorbent chamber and said dialyzer chamber, whereby dialysate fluid fed into the unit is distributed in a parallel flow through the dialyzer and the adsorbent chambers, whereby the apertures into the adsorbent chamber and the dialyzer chamber can be sized to obtain a greater volume of flow through the dialyzer chamber for better dialysis and a lesser volume of flow through the adsorbent chamber for better adsorption, and a large volume low pressure pump can be used for circulating the dialysate fluid.

2. A combined dialyzer and adsorber unit as claimed in claim 1 in which said core member is the adsorbent chamber, and said sleeve member is the dialyzer chamber having the dialyzer therein.

3. A combined dialyzer and adsorber unit as claimed in claim 1 in which said adsorbent chamber is a cylindrical chamber and said dialysate distribution chamber is mounted on the bottom thereof with the bottom wall of the cylindrical chamber having apertures from the distribution chamber to said adsorbent chamber, and said dialyzer chamber is an annular chamber having the lower end extending below the bottom of said adsorbent chamber and the apertures from said dialysate distribution chamber opening laterally from the dialysate distribution chamber into said dialyzer chamber.

4. A combined dialyzer and adsorber unit as claimed in claim 3 in which said dialyzer is a coil tube type dialyzer having a flat tube of a membrane material permeable to uremic wastes and toxic materials in blood, said tube being wrapped in a coil within said dialysate chamber around said core member, and a mesh material between each of the coils of the tube, and a blood inlet tube connected to one end of the flat tube and a blood outlet tube connected to the other end of the flat tube, the blood tubes extending to the exterior of said unit.

5. A combined dialyzer and adsorber unit as claimed in claim 1 in which said core member is the dialyzer chamber having the dialyzer therein and the sleeve member is the adsorbent chamber.

6. A combined dialyzer and adsorber unit as claimed in claim 1 further comprising a mass of adsorbent in said adsorbent chamber.

7. A combined dialyzer and adsorber unit comprising a core member in the form of an adsorbent chamber adapted to contain an adsorbent therein and having a dialysate outlet at one end of the unit, a sleeve member around said core member in the form of a dialyzer, and a dialysate distribution chamber on the other end of said unit having a dialysate inlet therein and having apertures opening onto said adsorbent chamber and having further apertures opening laterally of said unit for directing a flow of dialysate from the distribution chamber to a position just beneath the dialysate unit, whereby when the unit is stood on said other end in a tank of dialysate, dialysate fluid fed into the distribution chamber is distributed in a parallel flow through the adsorbent chamber and along the dialyzer on the outside of the adsorbent chamber, whereby the apertures into the adsorbent chamber and the dialyzer chamber can be sized to obtain a greater volume of flow through the dialyzer chamber for better dialysis and a lesser volume of flow through the adsorbent chamber for better adsorption, and a larger volume low pressure pump can be used for circulating the dialysate fluid.

8. A combined dialyzer and adsorber unit as claimed in claim 7 in which said adsorbent chamber is a cylindrical chamber having a support member depending from said other end for supporting the unit in a tank of dialysate.

9. A combined dialyzer and adsorber unit as claimed in claim 8 in which said support member is an annular member, and said further apertures extend through said annular member.

10. A combined dialyzer and adsorber unit as claimed in claim 7 in which said dialyzer is a capillary tube type dialyzer in which the capillary tubes extend in the direction around said adsorbent chamber.

11. A combined dialyzer and adsorber unit as claimed in claim 7 further comprising a mass of adsorbent in said adsorbent chamber.

* * * * *